United States Patent [19]

Katz et al.

[11] Patent Number: 5,035,618
[45] Date of Patent: Jul. 30, 1991

[54] INSTRUMENT FOR THE TREATMENT OF DENTAL ROOT-CANALS

[75] Inventors: Larry Katz, Valley Stream, N.Y.; Michel Maillefer; Pierre-Luc Maillefer, both of Ballaigues, Switzerland

[73] Assignee: Les Fils D'Auguste Maillefer, Societe Anonyme a Ballaigues, Switzerland

[21] Appl. No.: 487,586

[22] Filed: Mar. 2, 1990

[30] Foreign Application Priority Data

Mar. 21, 1989 [CH] Switzerland ............ 1.029/89

[51] Int. Cl.⁵ ............................... A61C 5/02
[52] U.S. Cl. ........................ 433/102; 433/165
[58] Field of Search ............ 433/102, 141, 142, 165, 433/166, 224

[56] References Cited

U.S. PATENT DOCUMENTS

| 2,453,696 | 11/1948 | Brooks | 433/165 |
| 4,190,958 | 3/1980 | Martin et al. | 433/102 |
| 4,299,571 | 11/1981 | McSpadden | 433/102 |
| 4,332,561 | 6/1982 | McSpadden | 433/102 |

FOREIGN PATENT DOCUMENTS

| 330173 | 8/1989 | European Pat. Off. | 433/102 |
| 2303148 | 7/1974 | Fed. Rep. of Germany | 433/165 |
| 379200 | 8/1932 | United Kingdom | 433/165 |

Primary Examiner—Gene Mancene
Assistant Examiner—Michael Lynch
Attorney, Agent, or Firm—Silverman, Cass & Singer, Ltd.

[57] ABSTRACT

The end of an instrument for the treatment of dental root-canals is coated with a layer of anti-friction material. The low coefficient of friction of the antifriction material and the fact that it renders the end of the instrument non cutting or non abrasive facilitates greatly the penetration of the instrument in the dental root-canal, especially when the canal is curved, and has the result that the instrument does not bite into the wall of the canal and does not exert thereon an action which is greater on the outside of the curve than on the inside thereof.

11 Claims, 1 Drawing Sheet

INSTRUMENT FOR THE TREATMENT OF DENTAL ROOT-CANALS

BACKGROUND OF THE INVENTION a) Field of the Invention

The present invention relates to an instrument for the treatment of dental root-canals, comprising a tapered stem.

b) Description of the Prior Art

The treatment of a dental root-canal starts with the extraction of the nerve which is followed by rectification of the canal to open out the latter. This rectification is effected mainly by means of drills, of reamers, of cleansers and/or of files used some of them by hand, and others with mechanical driving means having a rotatable or a back-and-forth movement, or also a vibratory movement. The rectification of a canal is not effected by means of only one instrument but by means of the successive use of several reamers or files, starting with the smallest ones and ending with the biggest ones.

The rectification of curved root-canals raises problems so far as the instrument has a tendency to penetrate into the wall of the canal which is at the outside of the curve instead of following this curve up to the end of the dental root (apex).

Moreover, even if the instrument follows the canal up to its end, it has a tendency to act more strongly on the wall situated at the outside of the curve or to form thereon shoulders which will render more difficult the introduction of the next-used instruments up to the bottom of the root, and the subsequent obturation of the canal by means of gutta-percha points or cement.

This problem has been only partially solved by the utilization of very flexible instruments or of instruments with a non-cutting rounded point which is smooth or flattened, as well as by means of a pre-curving of the instruments.

However, the flexibility of the instrument does not always prevent the instrument entering into the wall of the canal nor ensure that it does not deform the canal by rectifying more strongly the wall of the canal on the outer side of the curve.

So far as the instruments having a rounded flattened and smooth point are concerned, they are in practice difficult to manufacture, especially when it is a matter of very fine instruments.

SUMMARY OF THE INVENTION

The object of the present invention is to provide a instrument for the treatment of dental root-canals which does not present the foregoing drawbacks.

This object is achieved in accordance with the invention due to the fact that the end of the stem of the instrument is covered with a layer of antifriction material.

The various features of the invention will be apparent from the following description, drawings and claims, the scope of the invention not being limited to the drawings themselves as the drawings are only for the purpose of illustrating a way in which the principles of the invention can be applied. Other embodiments of the invention utilising the same or equivalent principles may be used and structural changes may be made as desired by those skilled in the art without departing from the present invention and the purview of the appended claims.

DESCRIPTION OF THE PREFERRED EMBODIMENT

Figures 1, 2:
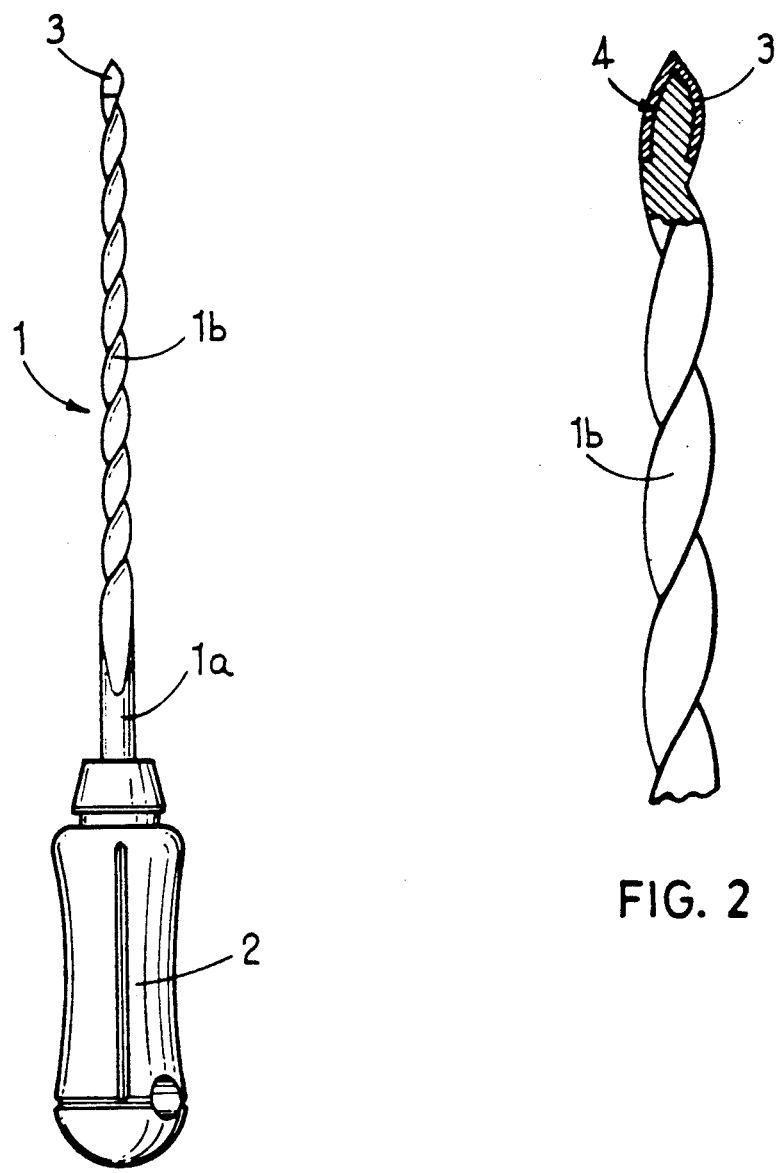
FIG. 1 is an elevational view of a file for the treatment of dental root-canals.
FIG. 2 is a sectional view of the end of this file, to a much enlarged scale.

The file represented comprises a tapered stem 1 inserted in a handle 2 and presenting, at its root, a smooth portion 1a followed by a cutting portion 1b. The point of this stem is coated at 3 with a layer of antifriction material the thickness of which is situated between some microns and 100 microns and which extends over a length varying from 0.5 to 3.0 mm.

The low coefficient of friction of the antifriction layer 3 and the fact that this layer makes the end of the instrument non cutting and non abrasive has the advantage of enabling the instrument to penetrate into dental root-canals, even when these canals are curved, without biting into the wall of the canal or exerting thereon an action which is greater on the outside of the curve than on the inside thereof.

In spite of the fact that the layer of antifriction material 3 is very thin, the end of the stem 1 is provided with an annular recess 4 (FIG. 2) the depth of which, which has been greatly exaggerated in the drawing, corresponds to the thickness of the layer of antifriction material, in which is located this layer. Thus, the layer 3 is flush with the stem 1 and the outer surface of the instrument does not show an annular shoulder in the region of the end of the layer 3.

The antifriction material used can be constituted by a self-lubricating material such as a two-component epoxy lacquer with the inclusion of self-lubricating particles, for instance oil particles, or a layer constituted by a plastic film made for example of polytetrafluorethylene (PTFE). It could also be constituted by a chemical coating of phosphorous nickel (NiP) for instance, or by a ionic coating (vector by plasma of neutral gas) such as titane nitride (TiN), titane carbide (Tic), zirconium oxide ($Z_rO_2$) or by a bioceramic made for instance of zirconium oxide and of yttrium oxide ($Z_rO_2/Y_2O_3$).

The invention is not restricted to files but can apply to all the instruments for the treatment of dental root-canals such as drills, reamers, cleansing or other tools, operated by hand or by a motor.

We claim:

1. An instrument for the treatment of dental canals, said instrument comprising a tapered stem, and a layer of anti-friction material by which an outer end of said stem is coated, the end of said stem including an annular recess the depth of which corresponds to the thickness of said layer and which is occupied by said layer.

2. An instrument as claimed in claim 1, in which the thickness of said layer is less than or equal to 100 microns.

3. An instrument as claimed in claim 1, in which said layer extends over a length in the range from 0.10 mm to 3.0 mm.

4. An instrument as claimed in claim 1, in which said layer is made of a self-lubricating material.

5. An instrument as claimed in claim 4, in which said layer is made of an epoxy lacquer including self-lubricating particles.

6. An instrument as claimed in claim 1, in which said layer is constituted by a plastic film.

7. An instrument as claimed in claim 6, in which said layer is constituted by a film of polytetrafluorethylene.

8. An instrument as claimed in claim 1, in which said layer is constituted by a chemical coating.

9. An instrument as claimed in claim 1, in which said layer is constituted by an ionic coating.

10. An instrument as claimed in claim 1, in which said instrument is flexible.

11. An instrument for the treatment of dental canals, said instrument comprising:
   an elongate stem having a substantially circular cross-sectional configuration and including first and second ends;
   said first end of said stem terminating in a reduced diameter tapered portion having a substantially pointed distal end and a proximal end having a predetermined diameter less than the diameter of said stem so that a shoulder is formed in said stem about the base of said proximal end of said tapered portion; and
   a layer of anti-friction material positioned about the periphery of said tapered portion of said first end of said stem for substantially rendering said tapered portion uncuttable, the thickness of said layer being selected to provide said tapered portion with a diameter substantially equal to the diameter of said stem so that a smooth transition is provided between the periphery of said stem and said layer of said tapered portion.

* * * * *